United States Patent [19]
Doi et al.

[11] 4,219,498
[45] Aug. 26, 1980

[54] PROCESS FOR PREPARING HIGHLY PURE-2-ACRYLAMIDO-2-METHYLPROPANESULFONIC ACID

[75] Inventors: Shunichi Doi; Masatake Kamogawa, both of Yokohama, Japan

[73] Assignees: Nitto Chemical Industry Co., Ltd.; Mitsubishi Rayon Co., Ltd., both of Tokyo, Japan

[21] Appl. No.: 8,113

[22] Filed: Jan. 31, 1979

[30] Foreign Application Priority Data

Jun. 12, 1978 [JP] Japan .................................. 53/69928

[51] Int. Cl.$^2$ ............................................ C07C 143/02
[52] U.S. Cl. ................................................ 260/513 N
[58] Field of Search ..................................... 260/513 N

[56] References Cited
PUBLICATIONS

Vogel, "Practical Org. Chem.," 3rd Ed. (1962), pp. 122–125.

*Primary Examiner*—A. Siegel
*Attorney, Agent, or Firm*—Cushman, Darby & Cushman

[57] ABSTRACT

This disclosure relates to a process for preparing highly pure 2-acylamido-2-methylpropanesulfonic acid, which comprises the steps of adding acetic acid to a slurry containing crystals of 2-acrylamido-2-methylpropanesulfonic acid obtained by the reaction of acrylonitrile, isobutene and either conc. sulfuric acid, fuming sulfuric acid or sulfuric anhydride plus water in a solvent, then distilling the resulting mixture to replace the reaction solvent with acetic acid, adding water or hydrous acetic acid to the resulting mixture, heating the mixture to dissolve said crystals, and subjecting the solution to recrystallization.

7 Claims, No Drawings

PROCESS FOR PREPARING HIGHLY PURE-2-ACRYLAMIDO-2-METHYLPROPANE-SULFONIC ACID

BACKGROUND OF THE INVENTION

1. Field of the Invention

This invention relates to a process for the efficient preparation of highly pure 2-acrylamido-2-methylpropanesulfonic acid.

2. Description of the Prior Art

2-Acrylamido-2-methylpropanesulfonic acid (hereinafter referred to simply as AMPS) to be purified according to this invention is a known compound which is prepared by the methods described in U.S. Pat. Nos. 3,506,707 and 3,544,597, British Pat. No. 1,090,779, West German Offenlegungsschrift No. 2,523,616, and Japanese Patent Publication No. 30,059/75.

In a preparative method typical of those described in the above patent publications, isobutene and fuming sulfuric acid are allowed to react in the presence of an excess of acrylonitrile, which is also used as reaction medium, and the resulting AMPS is allowed to precipitate directly from the reaction mixture. The crude crystals thus obtained are washed with acrylonitrile and, if necessary, recrystallized from a solvent.

Beside being used as an agent for improving the dyeing property of acrylic or other fibers, AMPS and its homologs can be polymerized to form useful homopolymers and copolymers. These polymers are useful as polyelectrolytes and are known to be usable as flocculant, dispersant, adhesive and fluidity regulator, and there are many patents in these fields.

The crude AMPS crystals as obtained by washing with a solvent the crystals precipitated directly from the reaction mixture may be used in some of the above-mentioned uses. However, in order to produce a polymer having a considerably high molecular weight, the crude crystals must be completely dissolved in a solvent and recrystallized therefrom.

For instance, the copolymer of AMPS and acrylamide for use as a mucilaginous material for papermaking and a flocculant must have a high molecular weight, and in order to produce such a high molecular weight copolymer, AMPS must have such a high purity as to be obtained by repeated recrystallization, otherwise no satisfactory result can be obtained.

The use of a copolymer of AMPS and acrylamide as a mucilaginous material for papermaking has been described in U.S. Pat. No. 3,772,142 and Japanese Pat. Application Kokai (Laid-Open) Nos. 59,507/75 and 27,808/77.

Regarding the function of a mucilaginous material for papermaking, Japanese Patent Application Kokai (Laid-Open) No. 27,808/77 states that "this function is to enable fibers of a pulp and the like to be dispersed in water, and the most important point is whether or not the mucilaginous material added only in a small amount to a fiber slurry in sheet formation can sufficiently control the rate of drainage; the practical usefulness of a mucilaginous material in controlling the rate of drainage is evaluated in terms of anti-freeness which corresponds to the spinnability of an aqueous solution of said mucilaginous material, said spinnability corresponding also to the amount of mucilaginous material used per unit weight of pulp in practical papermaking". The values of both spinnability and anti-freeness, which are defined hereinafter, increase with an increase in purity of AMPS used as a starting material. The larger the said values, the higher the molecular weight of the copolymer and the more favorable the effect on papermaking.

In purifying AMPS by recrystallization from a solvent, the type of solvent-purification methods is limited because AMPS is soluble in only water, lower alcohols and dimethylformamide. Moreover, water tends to cause polymerization and decomposition of AMPS at temperatures of 50° C. or more, while dimethylformamide is disadvantageous in that precipitation of crystals of AMPS is not easy and owing to its high boiling point the drying of precipitated crystals requires a long period of time. For these reasons, methanol seems to have been chiefly used as the solvent in conventional purification of AMPS by recrystallization, as described, for example, in British Pat. No. 1,090,779 and Japanese Patent Publication No. 30,059/75 in connection with compounds analogous to AMPS.

The recrystallization method in which methanol is used as solvent, however, presents also the problems that AMPS purified by the recrystallization method yields polymers having not sufficient performance characteristics and yield of recrystallization is unsatisfactory.

SUMMARY OF THE INVENTION

In order to solve the aforementioned problem, the present inventors have conducted research on the production of highly pure AMPS to find surprisingly that the substitution of acetic acid for the reaction medium after the completion of the synthetic reaction results in a highly pure AMPS crystals and that AMPS is stable in hydrous acetic acid.

According to this invention, there is provided a process for the efficient preparation of highly pure AMPS, which comprises adding acetic acid to a slurry containing crystals of AMPS obtained by the reaction of acrylonitrile (hereinafter referred to as AN), isobutene, and either conc. sulfuric acid, fuming sulfuric acid or sulfuric anhydride plus water (preferably fuming sulfuric acid) in a solvent, then distilling the resulting mixture to replace the reaction solvent with acetic acid, adding water or hydrous acetic acid to the mixture, heating the mixture to dissolve said crystals, and subjecting the solution to recrystallization.

In conventional methods for purifying AMPS, crude AMPS crystals directly precipitated out of the reaction mixture are first taken out of the reaction system, and then recrystallized from a solvent, whereas the process of this invention is characterized in that both the reaction and the purification are carried out in the same vessel and the separation, washing and drying of crystals are carried out in one series, resulting in a great reduction in equipment cost, labor cost, and materials cost as well as improvement in workability and productivity. Further, since the recrystallization is effected after crude AMPS crystals are dissolved in hydrous acetic acid, the crystals thus obtained are so sufficiently pure that the crystals can be used to produce a copolymer with acrylamide for a mucilaginous material for papermaking. When an excess of AN is used to serve as reaction medium, it follows that the AN is recovered by distillation in the presence of acetic acid after completion of the reaction. Owing to the polymerizing tendency of AN, the recovery of AN has hitherto had to be carried out by distillation under reduced pressure or under reflux of AN containing a polymerization inhibitor, however the AN can be efficiently recovered at atmospheric pressure without polymerization of AN according to the process of this invention. This is one of the characteristic features of this invention.

DETAILED DESCRIPTION OF THE INVENTION

As for the solvents in which to dissolve crude AMPS crystals in the reaction system and from which to recrystallize AMPS, it may be conceivable from the view point of dissolving AMPS to employ water, lower alcohols including methanol as representative, and dimethylformamide. However, methanol is unsuitable for the solvent replacement, because it has a boiling point lower than that of AN; ethanol and higher alcohols are unsuitable, because a large amount thereof is necessary owing to low solubility of AMPS in these solvents or it is impossible to obtain highly pure crystals from these solvents; and dimethylformamide is not usable, because crystallization is difficult owing to the too high solubility of AMPS in this solvent.

Water is unsuitable, because it reacts with the excess AN in the presence of sulfuric acid to form acrylamide, and AMPS has a very high tendency of polymerization. However, since easily polymerizable AMPS becomes stable to water in the presence of acetic acid as mentioned above therefore, an acetic acid-water system may be used in this invention as a solvent for dissolving crude AMPS crystals. After the reaction medium has been replaced by acetic acid, water is added to the slurry to dissolve AMPS crystals. Acetic acid containing the necessary amount of water can be used in place of water. Since the unreacted AN can react with water to form acrylamide as a by-product, it is preferably removed together with the reaction medium by distillation prior to the addition of water.

For the reasons mentioned above, as the solvent to be substituted for the reaction medium after completion of the reaction, acetic acid is selected. Another reason for selecting acetic acid is that recovery and purification of the solvent is easy because acetic acid does not form an azeotrope either with AN used as the reaction medium or with water. Thus, the replacing solvent used in this invention is limited to acetic acid.

Although the amount of acetic acid used is subject to no particular restriction, it is necessary to be of such a quantity that the mixture of AMPS crystals and acetic acid can be handled as a slurry without difficulty after removal of the reaction medium. Acetic acid is used in an amount of preferably 0.5 to 5 times, more preferably 1 to 3 times, the weight of reaction medium. A part of the acetic acid may be added together with water after the reaction medium has been replaced by acetic acid.

The amount of water or hydrous acetic acid used is that sufficient to dissolve completely the crystals in the slurry. In view of the yield of purified crystals, however, water is preferably used in an amount as small as possible, and said amount is such that the water content of acetic acid in the system ranges from 3 to 40% by weight.

As the reaction medium, there may be used inert solvents such as chlorinated hydrocarbons and ethers. In this case, however, the solvents must be such that the formed AMPS does not dissolve therein and precipitates therefrom. Examples of suitable reaction medium are 1,2-dichloroethane, carbon tetrachloride, and ethylene glycol dimethyl ether. These solvents have boiling points lower than that of acetic acid and, hence, are replaceable similarly to AN.

The replacement of the reaction medium with acetic acid can be effected by the removal of the former by atmospheric distillation, because AMPS has a quite high thermal stability in the presence of acetic acid.

After the solvent replacement, water is added to the system and the mixture is heated preferably at 60° to 110° C., more preferably at 80° to 90° C., to dissolve AMPS crystals. After completion of the dissolution, the solution is cooled to precipitate crystals. Beside the customary way of crystallization in which the change in solubility with a change in temperature is utilized, it is possible to improve the yield of recrystallization by decreasing the water content of acetic acid by distillation or by the addition of glacial acetic acid or acetic anhydride. The mixture is cooled to about 20° C. to precipitate sufficiently the crystals, then filtered to collect the crystals which are then washed with approximately the equal quantity of acetic acid and dried.

As described above, there are a number of conventional methods for preparing AMPS. A typical method comprises adding at a low temperature fuming sulfuric acid to an excess of AN, used to serve as a reaction medium, then introducing gaseous isobutene into the mixture to allow to react, then allowing the resulting AMPS to crystallize directly out of the reaction mixture, separating the crystals from the mother liquor, then washing the crystals with AN, and drying the washed crystals to obtain crude AMPS crystals. Conc. sulfuric acid or sulfuric anhydride plus water may be substituted for the fuming sulfuric acid in the known manner.

According to this invention, when crystallization of AMPS has been completed in the reaction mixture obtained by the above-noted typical method, acetic acid is added to the reaction mixture in an amount of about twice the weight of the reaction medium, and the AN which served as a reaction medium is removed by distillation. To the reaction mixture in the slurry form, in which AN has been thus replaced by acetic acid, is added at a temperature of 60° to 110° C. water in the amount necessary to dissolve completely the AMPS crystals. The slurry is treated at a temperature in the said range to dissolve the crystals. Immediately after the crystals have been dissolved, the solution is cooled to recrystallize AMPS. The crystals are separated from the mixture by, for example, centrifugation, washed with a slight amount of acetic acid and dried to obtain highly pure AMPS crystals.

A copolymer of the thus obtained AMPS and acrylamide showed a high spinnability and an excellent antifreeness and is quite suitable for a mucilagenous material for papermaking, a flocculant and other uses.

PREFERRED EMBODIMENT OF THE INVENTION

The invention is further illustrated below in detail with reference to Examples. In the Examples, the performance characteristics of copolymers were tested in the following manner on a copolymer prepared from the AMPS crystals obtained and acrylamide.

Polymerization:

In 900 cc of water were dissolved 15 g of AMPS and 85 g of acrylamide. After having been adjusted to pH 8, the solution was made up to 1,000 cc and charged into a polymerizer. To the polymerizer which has been thoroughly flushed with nitrogen were added 20 mg of potassium persulfate and 20 mg of dimethylaminopropionitrile. The polymerization was started at 35° C. and after 4 to 5 hours a maximum temperature of around 52° C. was attained. After 10 hours, the resulting polymer was discharged, allowed to cool, dried at 105° C. for 4 hours, and pulverized.

Spinnability (mm):

A 0.1% by weight aqueous solution of the dried polymer was prepared and the spinnability of the solution was measured in a constant temperature and humidity chamber at 20° C. and 65% RH in the following manner: A glass rod, 6 mm in diameter, was immersed in the solution to a depth of 10 mm and withdrawn at a rate of 500 mm/minute until the liquid thread was broken. The distance from the liquid level to the end of the glass rod was measured.

Anti-freeness (%):

To a 0.3% by weight slurry of a commercial NBKP (coniferous bleached kraft pulp) beaten to a Canadian standard freeness (JIS P 8121) of 300 ml was added 0.1% by weight (based on the pulp) of a copolymer. The drainage (V) of the resulting slurry was measured by means of a Canadian standard freeness tester and the anti-freeness was calculated by the following equation:

$$\text{Anti-freeness} = (300 - V)/V \times 100.$$

A higher anti-freeness is indicative of a higher effectiveness of the polymer used as a mucilanginous material for papermaking.

Viscosity (centipoise):

The viscosity of a 0.1% by weight aqueous solution of a copolymer was measured at 25° C. by using a Brookfield viscometer at 6 rpm.

EXAMPLE 1

Into a 1-liter glass reactor equipped with a stirrer, a distillation column and a gas inlet tube was charged 300 g of AN. To the reactor was added at 0° C. 56.4 g of 6%-fuming sulfuric acid (fuming sulfuric acid containing 6% of free $SO_3$; the same applies hereinafter). Into the resulting mixture was introduced 33.2 g of gaseous isobutene at a temperature of 50° C. or less. After completion of the introduction of isobutene, the mixture was kept with stirring at 50° C. for one hour to age the mixture. After addition of 400 g of acetic acid to the reaction mixture, unreacted AN which served as a reaction medium was removed by distillation. To the resulting mixture was added 40 g of water. On heating with stirring, the crystals were completely dissolved at 90° C. The solution was immediately cooled to precipitate AMPS crystals. After the mixture had been cooled to 20° C., the crystals were separated, washed twice with acetic acid corresponding in weight to about one-half of the crystals, and dried, to obtain 98 g of highly pure AMPS crystals, corresponding to a yield of 80% by weight based on isobutene.

The performance characteristics of a copolymer prepared by using the highly pure AMPS obtained above were as shown in the Table. The performance characteristics of copolymers prepared by using the crystals obtained in the following Examples were also shown in the same Table.

EXAMPLE 2

Into the same reactor as used in Example 1 was charged 300 g of AN. To the reactor was added at −10° C. 55.5 g of 13%-fuming sulfuric acid. Into the resulting mixture was introduced at a temperature of 50° C. or less 33.2 g of gaseous isobutene. After completion of the introduction of isobutene, 3 g of water was added to the mixture and the solution was aged by keeping it at 50° C. with stirring for one hour. To the reaction mixture was added 450 g of acetic acid. The unreacted AN which served as a reaction medium was removed by distillation. After addition of 50 g of water, the mixture was heated with stirring until the crystals had been completely dissolved at about 90° C. The solution was immediately cooled to crystallize AMPS. After cooling to 20° C., the crystals were separated, washed twice with acetic acid of the quantity corresponding to about one-half weight of the crystals, and dried, to obtain 100 g of highly pure AMPS crystals, corresponding to a yield of 82% by weight based on isobutene.

EXAMPLE 3

In a manner similar to that in Example 1, an AMPS slurry was obtained by reacting 94 g of AN, 56.4 g of 6%-fuming sulfuric acid, and 33.2 g of isobutene in the same reactor as used in Example 1 containing 250 g of 1,2-dichloroethane. After addition of 350 g of acetic acid to the reaction mixture, 1,2-dichloroethane which served as reaction medium and unreacted AN were removed by distillation. To the distillation residue was added 35 g of water and the mixture was heated with stirring until the crystals had been completely dissolved at about 90° C. The solution was cooled to room temperature and acetic anhydride was added thereto so that the water content of acetic acid may in the system became about 2% by weight. After cooling the mixture to 20° C., the precipitated AMPS crystals were separated, washed and dried, to obtain 86 g of highly pure AMPS, corresponding to a yield of 70% based on isobutene.

EXAMPLE 4

In a manner similar to that in Example 2, 83 g of highly pure AMPS was obtained by using ethylene glycol dimethyl ether as the reaction medium. The yield was 68% by weight based on isobutene.

COMPARATIVE EXAMPLE 1

Into the same glass reactor as used in Example 1 was charged 300 g of AN. To the reactor was added at 0° C. 56.4 g of 6%-fuming sulfuric acid. Into the resulting mixture was introduced at a temperature of 50° C. or less 33.2 g of gaseous isobutene. After completion of the introduction of isobutene, the mixture was aged by keeping it at 50° C. for one hour. After cooling the resulting slurry to 20° C., crystals were separated, washed twice with equal quantity of AN and dried, to obtain 110 g of AMPS crystals, corresponding to a yield of 90% by weight based on isobutene.

COMPARATIVE EXAMPLE 2

To 110 g of the AMPS crystals obtained in Comparative Example 1 were added 500 g of acetic acid and 50 g of water. The resulting mixture was heated with stirring until the crystals had been completely dissolved at about 90° C. The solution was cooled to 20° C. and the precipitated crystals were separated, washed twice with acetic acid of the quantity corresponding to one-half of the crystals, and dried.

COMPARATIVE EXAMPLE 3

In the same manner as in Example 1, acetic acid was added to the reaction mixture and the unreacted AN which served as the reaction medium was removed by distillation to replace it by the acetic acid. Thereafter, the mixture was heated at 90° C. with stirring in the absence of water. After having been kept at 90° C. for 15 minutes, the mixture was cooled to 20° C. The crystals were separated, washed with acetic acid of the quantity corresponding to one-half of the crystals, and dried.

Table

|  | Performance of copolymer | | |
| --- | --- | --- | --- |
|  | Viscosity (cps) | Spinnability (mm) | Anti-freeness (%) |
| Example 1 | 395 | 45 | 70 |
| Example 2 | 385 | 43 | 68 |
| Example 3 | 390 | 44 | 70 |
| Example 4 | 390 | 44 | 70 |
| Comparative Example 1 | Not measurable | | |
| Comparative Example 2 | 395 | 44 | 71 |
| Comparative Example 3 | 200 | 8 | — |

What is claimed is:

1. A process for preparing highly pure 2-acrylamido-2-methylpropanesulfonic acid, which comprises the steps of adding acetic acid to a slurry containing crystals of 2-acrylamido-2-methylpropanesulfonic acid obtained by the reaction of acrylonitrile, isobutene and either conc. sulfuric acid, fuming sulfuric acid or sulfuric anhydride plus water in a reaction medium, then distilling the resulting mixture to replace the reaction medium with the acetic acid, adding water or hydrous acetic acid, heating the mixture to dissolve said crystals, and subjecting the solution to recrystallization.

2. A process according to claim 1, wherein the slurry containing crystals of 2-acrylamido-2-methylpropanesulfonic acid is obtained by the reaction of acrylonitrile, isobutene and fuming sulfuric acid.

3. A process according to claim 1 or 2, wherein the reaction medium is acrylonitrile.

4. A process according to claim 1 or 2, wherein after the reaction medium has been replaced by the acetic acid, water or hydrous acetic acid is added so that the water content of the acetic acid in the system may become 3 to 40% by weight.

5. A process according to claim 1 or 2, wherein the temperature for the dissolution of the crystals of 2-acrylamido-2-methylpropanesulfonic acid is 60° to 110° C.

6. A process according to claim 1 or 2, wherein after the crystals of 2-acrylamido-2-methylpropanesulfonic acid have been dissolved, glacial acetic acid or acetic anhydride is added to the solution to decrease the water content of the hydrous acetic acid, thereby effecting recrystallization.

7. A process according to claim 1 or 2, wherein after the crystals of 2-acrylamido-2-methylpropanesulfonic acid have been dissolved, the water content of the hydrous acetic acid in the system is decreased by distillation to effect recrystallization.

* * * * *